United States Patent

Okawa

Patent Number: 5,183,912
Date of Patent: Feb. 2, 1993

[54] ORGANOPENTASILOXANE AND METHOD FOR ITS PREPARATION

[75] Inventor: Tadashi Okawa, Chiba, Japan

[73] Assignee: Dow Corning Toray Silicone Co., Ltd., Tokyo, Japan

[21] Appl. No.: 832,152

[22] Filed: Feb. 6, 1992

[30] Foreign Application Priority Data

Feb. 13, 1991 [JP] Japan .................................. 3-41270

[51] Int. Cl.$^5$ .............................. C07F 7/08; C07F 7/10; C07F 7/18
[52] U.S. Cl. .................................. 556/425; 556/423; 556/437; 556/439; 549/215
[58] Field of Search ................ 549/215; 556/423, 425, 556/439, 437

[56] References Cited

U.S. PATENT DOCUMENTS

| | | | |
|---|---|---|---|
| 4,208,503 | 6/1980 | Martin | 549/215 X |
| 4,618,689 | 10/1986 | Thaver et al. | 556/425 |
| 4,640,967 | 2/1987 | Eckberg | 549/215 X |
| 4,804,768 | 2/1989 | Quirh et al. | 549/215 |
| 4,902,739 | 2/1990 | Ona et al. | 549/215 X |
| 4,981,988 | 1/1991 | Schinohe et al. | 556/425 |
| 5,115,069 | 5/1992 | Motegi et al. | 549/215 |
| 5,118,777 | 6/1992 | Okawa | 556/425 X |

Primary Examiner—Paul F. Shaver
Attorney, Agent, or Firm—Alexander Weitz

[57] ABSTRACT

An organopentasiloxane having the formula $$A-R^1-SiMe_2(OSiMe_2)_3 OSiR^2{}_{(3-n)}(OR^2)_n$$

wherein Me denotes a methyl radical; A is a group selected from the group consisting of methacryloxy, glycidoxy and amino; $R^1$ is a divalent organic group selected from the group consisting of an alkylene group having at least 2 carbon atoms and an alkyleneoxyalkylene group; $R^2$ is independently selected from monovalent hydrocarbon groups free of aliphatically unsaturated bonds; and n is an integer having a value of 1 to 3, and methods for the preparation thereof, are disclosed.

16 Claims, No Drawings

ORGANOPENTASILOXANE AND METHOD FOR ITS PREPARATION

FIELD OF THE INVENTION

The present invention relates to novel organopentasiloxanes and to methods for their preparation. More specifically, the present invention relates to organopentasiloxanes which bear at least one silicon-bonded hydrocarbonoxy group at one molecular chain terminal and which bear a methacryloxy-containing, glycidoxy-containing or amino-containing alkylene or alkyleneoxyalkylene group at the other molecular chain terminal. The present invention also relates to methods for the preparation of the aforesaid organopentasiloxanes.

BACKGROUND OF THE INVENTION

The physical and other properties of composites made from organic resin(s) plus inorganic substance(s) can be modified and/or improved by silane compounds which contain both silicon-bonded hydrocarbonoxy and organofunctionalized (methacryloxy, glycidoxy, amino, etc.) alkylene or alkyleneoxyalkylene. This occurs because these silane compounds become interposed between the organic resin and inorganic substance due to the different properties of the organofunctional group and the silicon-bonded hydrocarbonoxy. These types of silane compounds are widely employed as silane coupling agents, and examples here are silane compounds with the following chemical formulas.

$$CH_2=C(CH_3)COO(CH_2)_3Si(OCH_3)_3$$

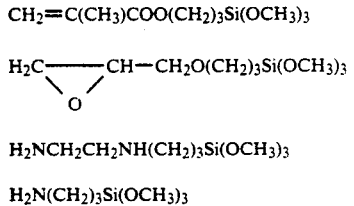

$$H_2NCH_2CH_2NH(CH_2)_3Si(OCH_3)_3$$

$$H_2N(CH_2)_3Si(OCH_3)_3$$

However, organopentasiloxane carrying organofunctionalized alkylene or alkyleneoxyalkylene at one molecular chain terminal and silicon-bonded hydrocarbonoxy at the other molecular chain terminal has been heretofore unknown.

SUMMARY OF THE INVENTION

The present invention takes as its object the introduction of a novel organopentasiloxane having the following formula

wherein Me hereinafter denotes a methyl radical; the group A is an organofunctional group selected from the group consisting of methacryloxy, glycidoxy and amino; $R^1$ is selected from the group consisting of an alkylene group having at least 2 carbon atoms and an alkyleneoxyalkylene group; $R^2$ is a single species or multiple species of monovalent hydrocarbon group free of aliphatically unsaturated bonds; and n is an integer having a value of 1 to 3.

The present invention further relates to methods for the preparation of the novel organopentasiloxane.

DETAILED DESCRIPTION OF THE INVENTION

The organopentasiloxane according to the present invention has the formula

In this formula, the group A is an organofunctional group selected from the group consisting of methacryloxy, glycidoxy and amino. The group $R^1$ is an alkylene group having at least 2 carbon atoms or is an alkyleneoxyalkylene group, and concrete examples thereof are alkylene groups, such as ethylene, propylene, butylene, pentylene and hexylene and alkyleneoxyalkylene groups, such as ethyleneoxypropylene and ethyleneoxybutylene. The group $R^2$ is independently selected from monovalent hydrocarbon groups free of aliphatically unsaturated bonds, or halo-substituted versions thereof. Specific examples of this group are alkyl groups such as methyl, ethyl, propyl, butyl, pentyl and hexyl; aryl groups such as phenyl, tolyl and xylyl; aralkyl groups such as benzyl and phenethyl; and substituted alkyl groups such as chloroethyl and 3,3,3-trifluoropropyl. $R^2$ is preferably methyl or ethyl from the standpoints of ease of synthesis, economics, and reactivity of the Si-bonded hydrocarbonoxy group. The methyl group is particularly preferred. The subscript n in the preceding formula is an integer with a value of 1 to 3, inclusive. Thus, the organopentasiloxane according to the present invention contains one Si-bonded hydrocarbonoxy group at one molecular chain terminal when n=1, two Si-bonded hydrocarbonoxy groups at one molecular chain terminal when n=2, and three Si-bonded hydrocarbonoxy groups at one molecular chain terminal when n=3. The organopentasiloxane according to the present invention differs from the prior silane compounds in that the hydrocarbonoxy group and organofunctionalized alkylene (or alkyleneoxyalkylene) are not bonded to the same silicon atom in the instant case. Rather, a highly flexible siloxane chain separates the silicon atom carrying the organofunctionalized (alkyleneoxy)alkylene group from the hydrocarbonoxy-bearing silicon atom, and the reactivities of the organofunctional group and Si-bonded hydrocarbonoxy are therefore not diminished or impaired.

The methacryloxy-containing or glycidoxy-containing organopentasiloxane according to the present invention can be prepared by an addition reaction in the presence of a platinum-type catalyst between organopentasiloxane with the formula

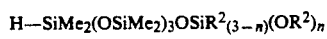

wherein $R^2$ and n have their previously defined meanings, and methacryloxy-containing or glycidoxy-containing alkene or methacryloxy-containing or glycidoxy-containing alkyleneoxyalkene.

One preparative method utilizes a platinum-type catalyst to promote the addition reaction between the silicon-bonded hydrogen and the alkene or alkyleneoxyalkene. Specific examples in this regard are chloroplatinic acid, alcohol solutions of chloroplatinic acid, platinum black, platinum-on-active carbon, platinum-olefin complexes and platinum-alkenylsiloxane complexes. Besides these platinum-type compounds, the first preparative method according to the present invention can employ other compounds which accelerate the aforesaid addition reaction, for example, complexes of Group VIII transition metals. The platinum-type catalyst should be added in the customary catalytic quantities, and preferably is added to give 0.1 to 500 ppm (parts per million) platinum in the platinum-type catalyst referred to the total quantity of organopentasiloxane plus methacryloxy- (or glycidoxy-) containing alkene or alkyleneoxyalkene in the reaction system.

The organopentasiloxane employed in the first preparative method according to the present invention has the formula $$HSiMe_2(OSiMe_2)_3OSiR^2_{(3-n)}(OR^2)_n$$

and is the main starting material for the organopentasiloxane according to the present invention and can be prepared by the following method. First, a dimethylhalosilane having the formula $$H-SiMe_2-X$$

wherein $X=$fluorine, chlorine, bromine, or iodine, is reacted at room temperature with hexamethylcyclotrisiloxane in a polar aprotic solvent, such as acetonitrile or dimethylformamide. After completion of the reaction, the alpha-halooctamethyltetrasiloxane reaction product with the following formula is recovered by distillation:

$$H-SiMe_2(OSiMe_2)_3-X$$

Then, this alpha-halooctamethyltetrasiloxane is hydrolyzed to afford alpha-hydroxyoctamethyltetrasiloxane of the following formula:

$$H-SiMe_2(OSiMe_2)_3-OH$$

This hydrolysis reaction must be run very carefully in order to prevent condensation reactions between the newly produced hydroxyl groups. Thus, for example, it is recommended that the alpha-halooctamethyltetrasiloxane be hydrolyzed in dilute aqueous base solution while cooling.

Finally, the alpha-hydroxyoctamethyltetrasiloxane is condensed with the following hydrocarbonoxysilane $$R^2_{(3-n)}Si(OR^2)_{(n+1)}$$

wherein $R^2$ and n have their previously defined meanings, to afford the target organopentasiloxane having the following formula:

$$H-SiMe_2(OSiMe_2)_3OSiR^2_{(3-n)}(OR^2)_n$$

This condensation reaction is run by mixing the two reactants with heating, and a catalyst is preferably used in order to accelerate the reaction. Preferred catalysts are exemplified as follows: carboxylic acids, such as acetic acid, propionic acid and acrylic acid; inorganic acids, such as carbonic acid, hydrochloric acid and sulfuric acid; inorganic bases, such as sodium hydroxide, potassium hydroxide and lithium hydroxide; and amines, such as triethylamine, pyridine, piperidine, quinoline and diethylhydroxylamine. Acetic acid and propionic acid are particularly preferred for their high catalytic activity, ease of removal after the reaction and relative freedom from secondary reactions such as siloxane chain cleavage reactions. The condensation reaction under consideration is preferably run in the temperature range of 70° to 130° C. A satisfactory reaction rate is not obtained at below about 70° C. while secondary reactions originating with siloxane chain cleavage occur at above about 130° C. Moreover, this condensation reaction is preferably run by distilling the alcohol by-product from the reaction system, both in order to shift the chemical equilibrium to the product side and in order to suppress condensation of the alcohol by-product with the alpha-hydroxyoctamethyltetrasiloxane. The molar ratio of alpha-hydroxyoctamethyltetrasiloxane to hydrocarbonoxysilane is not specifically restricted except that the latter component should be present in excess. However, in order to shift the chemical equilibrium to the product side and in order to suppress condensation between the alpha-hydroxyoctamethyltetrasiloxane and the alcohol by-product from the condensation reaction. 3 to 10 times as much hydrocarbonoxysilane, on a molar basis, should be used as alpha-hydroxyoctamethyltetrasiloxane. After completion of the reaction, the target organopentasiloxane having the following formula can be recovered by distillation of the reaction product $$H-SiMe_2(OSiMe_2)_3OSiR^2_{(3-n)}(OR^2)_n$$

wherein $R^2$ and n have their previously described meanings.

The methacryloxy- (or glycidoxy-) containing alkenes and methacryloxy- (or glycidoxy-) containing alkyleneoxyalkenes used in the first preparative method according to the present invention are concretely exemplified by methacryloxy-containing alkenes, such as methacryloxyethene, methacryloxypropene and methacryloxybutene; by methacryloxy-containing alkyleneoxyalkenes, such as methacryloxyethyleneoxypropene and methacryloxyethyleneoxybutene; by glycidoxy-containing alkenes, such as glycidoxyethylene, glycidoxypropene and glycidoxybutene; and by glycidoxy-containing alkyleneoxyalkenes, such as glycidoxyethyleneoxypropene and glycidoxyethyleneoxybutene. In the case of use of methacryloxy-containing alkene or alkyleneoxyalkene in the preparative method according to the present invention, a polymerization inhibitor (e.g., phenothiazine, hydroquinone monomethyl ether, tert-butylcatechol) is preferably added to the reaction system in order to inhibit free radical polymerization of the methacryloxy group. In the particular case of the reaction of methacryloxypropene, propene elimination occurs and the methacryloxysilyl ester is produced as a by-product. For this reason, it is recommended in this case that the obtained reaction mixture be subjected to alcoholysis in low-boiling alcohol solvent, e.g., methanol, followed by distillation. The use of methacryloxyethyleneoxypropene is preferred in order to suppress this secondary reaction. No specific restriction is placed on the quantity of addition of this methacryloxy- (or glycidoxy-) containing alkene or alkyleneoxyalkene with the proviso that this reagent should be added in at least an equimolar quantity referred to the starting organopentasiloxane.

The aforesaid organopentasiloxane is addition reacted with the aforesaid methacryloxy- (or glycidoxy-) containing alkene or alkyleneoxyalkene in the presence of the platinum-type catalyst also as described above. This reaction may be conducted in a solventless system, but it can also be run in a solvent. Useable solvents in this context are exemplified by aromatic solvents, such as benzene, toluene and xylene; aliphatic solvents, such as hexane and heptane; ether solvents, such as tetrahydrofuran and diethyl ether; ketone solvents, such as acetone and methyl ethyl ketone; ester solvents, such as ethyl acetate and butyl acetate; chlorinated hydrocarbon solvents, such as carbon tetrachloride, trichloroethane and chloroform; as well as dimethylformamide and dimethyl sulfoxide. While this addition reaction can be run at room temperature, it is preferably generally run in the temperature range of approximately 50° to 200° C.

The amino-containing organopentasiloxane according to the present invention can be prepared by an addition reaction in the presence of a platinum-type catalyst between organopentasiloxane with the formula

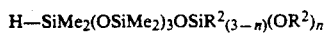

wherein $R^2$ and n have their previously defined meanings, and triorganosilylamino-containing alkene or triorganosilylamino-containing alkyleneoxyalkene and by subjecting the reaction product therefrom to a desilylation reaction. This second preparative method according to the present invention is explained in greater detail below.

Both the platinum-type catalyst and the organopentasiloxane $H-SiMe_2(OSiMe_2)_3OSiR^2_{(3-n)}(OR^2)_n$ employed in the second preparative method according to the present invention are the same as those explained above in detail for the first preparative method.

The triorganosilylamino-containing (alkyleneoxy)alkene employed by the second preparative method according to the present invention is concretely exemplified by triorganosilylamino-containing alkenes, such as trimethylsilylaminoethene, trimethylsilylaminopropene, trimethylsilylaminobutene, triethylsilylaminoethylene and dimethylethylsilylaminopropene; and by triorganosilylamino-containing alkyleneoxyalkenes, such as trimethylsilylaminoethyleneoxypropene and trimethylsilylaminoethyleneoxybutene. This triorganosilylamino-containing (alkyleneoxy)alkene should be added in at least an equimolar quantity based on the starting organopentasiloxane, but its quantity of addition is not otherwise restricted.

The aforesaid organopentasiloxane is addition reacted with the aforesaid triorganosilylamino-containing (alkyleneoxy)alkene in the presence of the platinum-type catalyst as described above. This reaction may be conducted in a solventless system as described for the first preparative method according to the present method, but it may also be run in a solvent. The solvents listed above serve as examples of solvents which may be used in this reaction. The addition reaction under consideration may be run at room temperature, but it is preferably generally run in the temperature range of approximately 50° to 200° C. In order to subject the reaction product to the desilylation reaction, the reaction product is first purified by distillation and is then subjected to alcoholysis in an alcohol solvent. The solvent used here is preferably methanol in order to facilitate purification of the organopentasiloxane according to the present invention after the desilylation reaction.

Because the organopentasiloxane according to the present invention carries both silicon-bonded hydrocarbonoxy and organofunctionalized alkylene or alkyleneoxyalkylene, it can be employed as a coupling agent in the same manner as silane coupling agents. For example, it may be used to treat the surface of inorganic fillers for plastics, to treat the surface of reinforcing fillers for silicone rubbers, as a primer to promote bonding and adhesion and as an adhesion-promoting agent.

EXAMPLES

The present invention is explained below through the use of illustrative examples.

REFERENCE EXAMPLE 1

One mole (94.6 Grams) of dimethylchlorosilane, 222.5 g (1 mole) of hexamethylcyclotrisiloxane, 6.8 g of dimethylformamide, and 68 g of acetonitrile were introduced into a stirrer-equipped four-neck flask. After stirring at room temperature for 1 hour, distillation in vacuo afforded 195.9 g of a product which was confirmed to be alpha-chlorooctamethyltetrasiloxane with the following structure based on the results of infrared absorption analysis (IR) and nuclear magnetic resonance analysis (NMR):

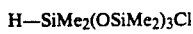

wherein Me hereinafter denotes a methyl radical.

Five hundred mL of water, 500 g of ice, 270 mL of diethyl ether, and 39.7 g (473.3 mmoles) of sodium bicarbonate were then introduced into a stirrer-equipped four-neck flask and cooled to 0° C. A solution of 110 g (347.0 mmoles) of the aforesaid alpha-chlorooctamethyltetrasiloxane in 100 mL of diethyl ether was dripped in from an addition funnel with stirring. After the completion of addition, the ether layer was separated and washed with water. Removal of the ether at room temperature in vacuo gave 97.5 g of product which was confirmed to be the alpha-hydroxyoctamethyltetrasiloxane with the following structure based on the results from IR and NMR:

Eighty Grams (267.9 mmoles) of the aforesaid alpha-hydroxyoctamethyltetrasiloxane, 122 g of tetramethoxysilane, and 0.0304 mL of propionic acid were introduced into a four-neck flask equipped with a stirrer and distillation set-up and were heated to 130° C. A mixture of tetramethoxysilane and methanol by-product was distilled from the system and fresh tetramethoxysilane was then supplied. The progress of the reaction was monitored by gas chromatography (GLC), and the process was repeated until the tetramethoxysilane peak had disappeared. A total of approximately 300 g of tetramethoxysilane was used. After completion of the reaction, 79.8 g of product was recovered by distillation in vacuo and collection of the fraction at 83°–89° C./1 mm Hg. This product was confirmed to be organopentasiloxane with the following structural formula according to the results from IR and NMR:

REFERENCE EXAMPLE 2

Ethylene glycol monoallyl ether (25.83 Grams; 252.9 mmoles), 40.3 g (398.3 mmoles) of triethylamine, and 50 mL of n-hexane were introduced into a four-neck flask equipped with a stirrer and distillation set-up and cooled with ice water to below 10° C. A solution of 27.8 g (265.5 mmoles) of methacryloyl chloride in 30 mL of n-hexane was dripped in while stirring, and the reaction was stirred for another 15 minutes at room temperature. At this point, the GLC peak for the ethylene glycol monoallyl ether had disappeared and the reaction was assumed to be finished. Two hundred ppm of phenothiazine (based on methacryloyl chloride) was added as polymerization inhibitor. Distillation in vacuo then afforded a colorless, transparent liquid, which was confirmed by NMR and IR to be allyloxyethyl methacrylate.

EXAMPLE 1

Twenty five Grams (59.7 mmoles) of the organopentasiloxane synthesized in Reference Example 1, having the structure $H-SiMe_2(OSiMe_2)_3OSi(OMe)_3$, 8.2 g (71.6 mmoles) of allyl glycidyl ether and platinum/tetramethyldivinyldisiloxane complex (quantity of platinum metal in the complex=20 ppm based on the total of the first two reagents) were introduced. A sample was taken after heating for 30 minutes at 70° to 100° C. The peak for the starting pentasiloxane had disappeared in GLC analysis while disappearance of the absorption characteristic of the SiH group was confirmed in IR. The product (27.9 g) was recovered by distillation in vacuo and collection of the fraction at 153°-157° C./1 mm Hg. IR and NMR confirmed this product to be pentasiloxane with the following structural formula:

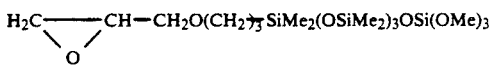

EXAMPLE 2

Twenty five Grams (59.7 mmoles) of organopentasiloxane synthesized in Reference Example 1, 13.5 g (89.5 mmoles) of trimethylsilylallylamine, and platinum/tetramethyldivinyldisiloxane complex (quantity of platinum metal in the complex=20 ppm based on the total of the first two reagents) were introduced. A sample was taken after heating for 30 minutes at 70° to 90° C. The peak for the starting organopentasiloxane had disappeared in GLC analysis while disappearance of the absorption characteristic of the SiH group was confirmed in IR. The product (25.1 Grams) was recovered by distillation in vacuo and collection of the fraction at 137°-144° C./1 mm Hg. IR and NMR confirmed this product to be organopentasiloxane with the following structural formula: $Me_3SiNH(CH_2)_3-SiMe_2(OSiMe_2)_3OSi(OMe)_3$ Twenty grams (42.0 mmoles) of this organopentasiloxane and 13.4 g (420.2 mmoles) of methanol were introduced and heated under reflux for 1 hour. The fraction at 110°-120° C./1 mm Hg was collected by distillation in vacuo to afford 9.9 g of product. This product was confirmed to be organopentasiloxane with the following structural formula based on the results from NMR and IR:

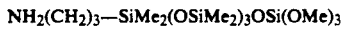

EXAMPLE 3

Allyl methacrylate (0.6 Grams; 5.26 mmoles) was mixed with 0.1 mg of phenothiazine and 5 mL of hexane, and platinum/tetramethyldivinyldisiloxane complex (quantity of platinum metal in the complex=20 ppm based on allyl methacrylate) was then introduced. A solution of 2 g (4.8 mmoles) of organopentasiloxane synthesized in Reference Example 1 in 1 mL of hexane was dripped in while heating under reflux. A sample was taken after heating for another 30 minutes under reflux. The peak for the starting organopentasiloxane had disappeared in GLC analysis while disappearance of the absorption characteristic of the SiH group was confirmed in IR. The solvent and low boilers were distilled out by heating in vacuo to give 2.2 g of product. This product was heated for 1 hour under reflux with 10 g of methanol in order to methanolyze the silyl ester by-product. The methanol and by-products were distilled out by heating in vacuo, and 1.0 g product was recovered. The product was confirmed by IR and NMR to be organopentasiloxane with the following structural formula:

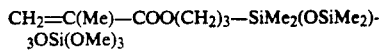

EXAMPLE 4

Allyloxyethyl methacrylate (2.23 Grams; 13.1 mmoles) as synthesized in Reference Example 2 was mixed with 0.4 mg of phenothiazine and 5 mL of hexane, and platinum/tetramethyldivinyldisiloxane complex (quantity of platinum metal in the complex=20 ppm based on allyloxyethyl methacrylate) was then introduced. A solution of 5 g (11.9 mmoles) of organopentasiloxane synthesized in Reference Example 1 in 5 mL of hexane was dripped in while heating under reflux. A sample was taken after heating for another 2 hours under reflux. The peak for the starting pentasiloxane had disappeared in GLC analysis while disappearance of the absorption characteristic of the SiH group was confirmed in IR. The solvent and low boilers were distilled out by heating in vacuo to give 6.8 g of product. This product was confirmed by IR and NMR to be pentasiloxane with the following structural formula:

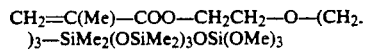

That which is claimed is:

1. An organopentasiloxane having the formula

wherein Me denotes a methyl radical; A is selected from the group consisting of methacryloxy, glycidoxy and amino radicals; $R^1$ is a divalent organic group selected from the group consisting of an alkylene group having at least 2 carbon atoms and an alkyleneoxyalkylene group; $R^2$ is independently selected from monovalent hydrocarbon groups free of aliphatically unsaturated bonds; and n is an integer having a value of 1 to 3.

2. The organopentasiloxane of claim 1, wherein $R^1$ is selected from the group consisting of ethylene, propylene, butylene, pentylene, hexylene, ethyleneoxypropylene and ethyleneoxybutylene groups.

3. The organopentasiloxane of claim 2, wherein wherein $R^2$ is independently selected from alkyl radicals having 1-6 carbon atoms.

4. The organopentasiloxane of claim 3, wherein each $R^2$ is a methyl radical.

5. The organopentasiloxane of claim 4, wherein $R^1$ is a propylene group.

6. The organopentasiloxane of claim 5, wherein A is a methacryloxy group.

7. The organopentasiloxane of claim 5, wherein A is a glycidoxy group.

8. The organopentasiloxane of claim 5, wherein A is an amino group.

9. The organopentasiloxane of claim 1, wherein n is 3.

10. The organopentasiloxane of claim 9, wherein wherein each $R^2$ is a methyl radical.

11. The organopentasiloxane of claim 10, wherein $R^1$ is a propylene group.

12. The organopentasiloxane of claim 11, wherein A is a methacryloxy group.

13. The organopentasiloxane of claim 11, wherein A is a glycidoxy group.

14. The organopentasiloxane of claim 11, wherein A is an amino group.

15. A method for the preparation of an organopentasiloxane having the formula $A'-R^1-SiMe_2(OSiMe_2)_3OSiR^2_{(3-n)}(OR^2)_n$, wherein Me denotes a methyl radical; A' is selected from the group consisting of methacryloxy and glycidoxy radicals; $R^1$ is a divalent organic group selected from the group consisting of an alkylene group having at least 2 carbon atoms and an alkyleneoxyalkylene group; $R^2$ is independently selected from monovalent hydrocarbon groups free of aliphatically unsaturated bonds; and n is an integer having a value of 1 to 3, which is characterized by an addition reaction, in the presence of a platinum-type catalyst, between an organopentasiloxane having the formula $H-SiMe_2(OSiMe_2)_3OSiR^2_{(3-n)}(OR^2)_n$, wherein $R^2$ and n have their previously defined meanings, and a functional alkene selected from the group consisting of methacryloxy-containing alkene, glycidoxy-containing alkene, methacryloxy-containing alkyleneoxyalkene and glycidoxy-containing alkyleneoxyalkene.

16. A method for the preparation of an organopentasiloxane having the formula $A''-R^1-SiMe_2(OSiMe_2)_3OSiR^2_{(3-n)}(OR^2)_n$, wherein Me denotes a methyl radical; A'' is an amino group; $R^1$ is a divalent organic group selected from the group consisting of an alkylene group having at least 2 carbon atoms and an alkyleneoxyalkylene group; $R^2$ is independently selected from monovalent hydrocarbon groups free of aliphatically unsaturated bonds; and n is an integer having a value of 1 to 3, which is characterized by an addition reaction, in the presence of a platinum-type catalyst, between an organopentasiloxane having the formula $H-SiMe_2(OSiMe_2)_3OSiR^2_{(3-n)}(OR^2)_n$, wherein $R^2$ and n have their previously defined meanings, and an alkene selected from the group consisting of triorganosilylamino-containing alkene and triorganosilylamino-containing alkyleneoxyalkene and thereafter subjecting the reaction product therefrom to a desilylation reaction.

* * * * *